United States Patent [19]

Nemeth et al.

[11] 4,097,627

[45] Jun. 27, 1978

[54] DOUBLE FACED TAB FASTENER CHARACTERIZED BY A STRIP OF RELEASE AGENT DESIGNED TO EXTEND PARTLY BEYOND THE WIDTH OF A STRIP OF ADHESIVE

[75] Inventors: Suzette B. Nemeth, Painesville; David W. Wilson, Mentor, both of Ohio

[73] Assignee: Avery International Corporation, San Marino, Calif.

[21] Appl. No.: 743,640

[22] Filed: Nov. 22, 1976

[51] Int. Cl.² ............... A41B 13/02; A61F 13/16; B32B 7/06; B32B 7/14
[52] U.S. Cl. .................. 428/40; 24/73 VA; 24/DIG. 11; 128/284; 128/287; 428/189; 428/352; 428/354
[58] Field of Search ............... 128/287, 284; 428/40, 428/189, 352, 354; 24/DIG. 11, 73 VA

[56] References Cited

U.S. PATENT DOCUMENTS

| | | | |
|---|---|---|---|
| 2,565,509 | 8/1951 | Marcin | 428/40 |
| 3,032,181 | 5/1962 | Hutter et al. | 428/352 |
| 3,808,718 | 5/1974 | Christiansen | 40/2 R |
| 3,926,190 | 12/1975 | Tritsch | 128/287 |
| 3,930,503 | 1/1976 | Tritsch | 128/287 |
| 3,955,576 | 5/1976 | Safford | 128/287 |
| 4,020,842 | 5/1977 | Richman et al. | 128/287 |

*Primary Examiner*—J.C. Cannon
*Attorney, Agent, or Firm*—McNenny, Pearne, Gordon, Gail, Dickinson & Schiller

[57] ABSTRACT

Diaper tab stock comprises a unitary substrate extending, transversely to machine direction, along first and second endward length portions separated by a third intermediate length portion, with adhesive on its topside at the first endward length portion, on its bottom side at the second endward length portion, and on neither side at the third intermediate length portion which separates the other two. A release coating on the bottom side of the first length portion extends partly onto the intermediate third length portion but stops short of the second length portion.

In a preferred method of manufacture and use, a release coating on the top side of the second length portion serves as a releasing support both for the adhesive which ends up on the bottom side of the second length portion and then for the adhesive on the first length portion when the first length portion is folded onto the second length portion.

3 Claims, 6 Drawing Figures

U.S. Patent     June 27, 1978     4,097,627
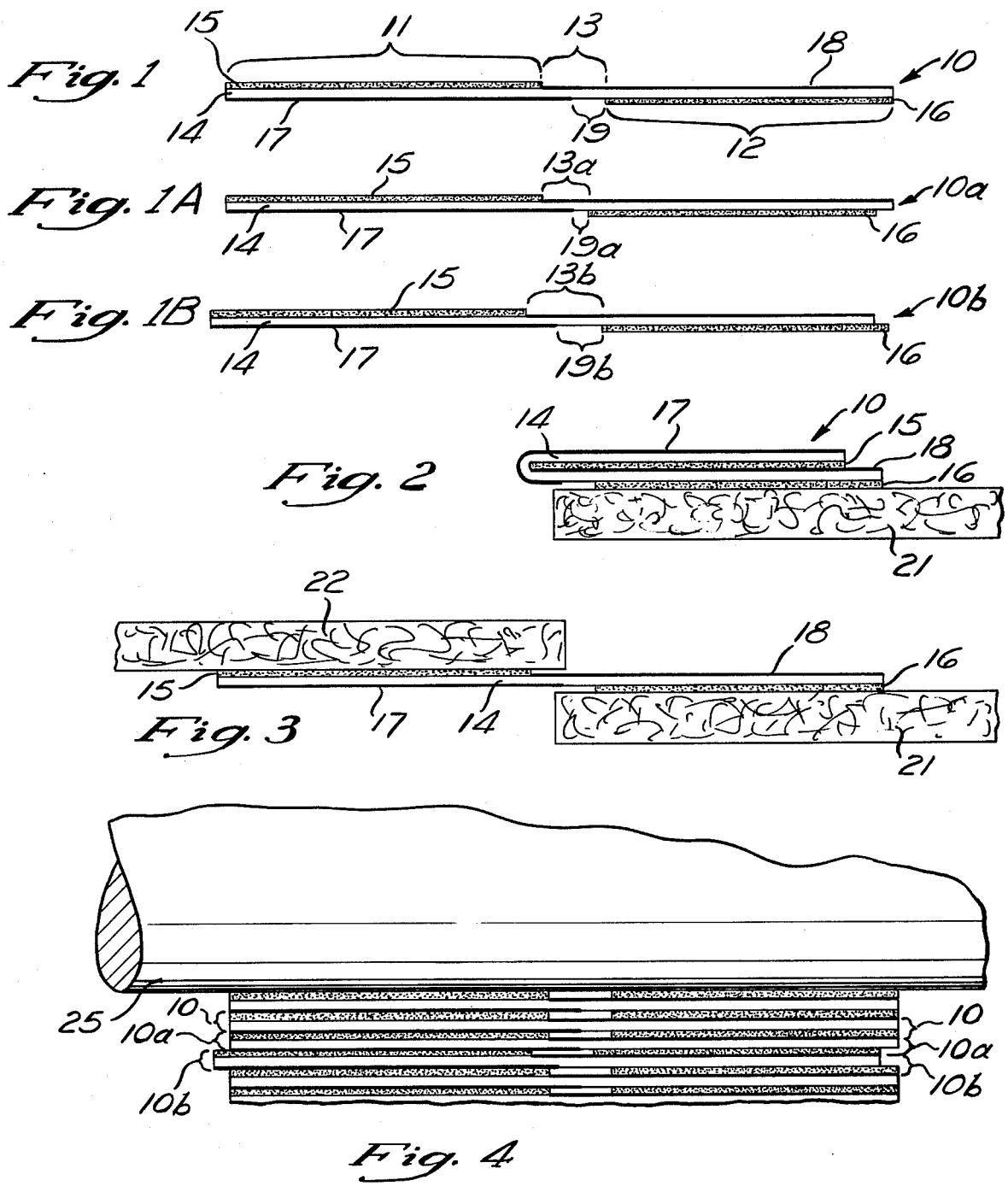

DOUBLE FACED TAB FASTENER CHARACTERIZED BY A STRIP OF RELEASE AGENT DESIGNED TO EXTEND PARTLY BEYOND THE WIDTH OF A STRIP OF ADHESIVE

This invention relates to laminate web constructions of linerless tab stock of the kind adapted to be supplied to a diaper manufacturer and to be separated by the manufacturer into individual diaper tab constructions and applied to individual diapers, usually two tabs to a diaper. By linerless is meant the absence of any adhesive-protecting liner of release paper or the like that has to be separately disposed of by the person applying the diaper.

Various prior art proposals for linerless constructions have been made including those shown in Safford U.S. Pat. No. 3,955,576 issued to Kimberly-Clark Corporation and Richman et al. application Ser. No. 624,870, filed Oct. 23, 1975, of common assignee with the present application. Still other forms of linerless tabs or linerless tab stock are shown in the following U.S. patents:

| | | | |
|---|---|---|---|
| 3,833,456 | 9/1974 | Reed et al. | Avery Products Corporation |
| 3,848,594 | 11/1974 | Buell | The Procter & Gamble Company |
| 3,853,129 | 12/1974 | Kozak | Union Carbide Corporation |
| 3,874,386 | 4/1975 | Kozak | Union Carbide Corporation |
| 3,893,460 | 7/1975 | Karami | Colgate-Palmolive Company |
| 3,901,239 | 8/1975 | Tritsch | Johnson & Johnson |
| 3,926,190 | 12/1975 | Tritsch | Johnson & Johnson |
| 3,930,502 | 1/1976 | Tritsch | Johnson & Johnson |
| 3,930,503 | 1/1976 | Tritsch | Johnson & Johnson |
| 3,943,609 | 3/1976 | Egan, Jr. | Colgate-Palmolive Company |
| 3,948,258 | 4/1976 | Karami | Colgate-Palmolive Company |
| 3,948,268 | 4/1976 | Karami | Colgate-Palmolive Company |
| 3,948,267 | 4/1976 | Karami | Colgate-Palmolive Company |

These constructions all employ considerable lengths of substrate which do not bear adhesive that attaches directly to the diaper, and which therefore do not contribute directly to the adhesive closure function. For example, Tritsch U.S. Pat. No. 3,926,190 employs an extra length of substrate 20 which does not bear adhesive but which is comparable in length to the two endmost adhesive bearing portions of the substrate. Kozak U.S. Pat. No. 3,853,129 has a middle segment 14 of his substrate which has been rendered non-adhesive by a covering plastic material 16 and which is comparable in length to the endmost adhesive bearing portions. Kozak U.S. Pat. No. 3,874,386 has intermediate nonadhesive sections 14 or 23 which individually or collectively compare in length with the adhesive-coated segments of the substrate associated with each end of the construction. Tritsch U.S. Pat. No. 3,903,503 also has a relatively long uncoated center section 17.

The remaining patents listed above generally have constructions wherein one or two substrates or large parts thereof do not bear adhesive, or bear adhesive that does not ultimately attach directly to parts of the diaper. Safford is an exception in that virtually the entire length of his construction, comprising two substrates, bears adhesive which ultimately attaches to the diaper except for a tiny intermediate substrate-to-substrate fastening portion. However Safford teaches that it is necessary to resort to a two-substrate construction for a practical product because of difficulties associated with attempting to make a single-substrate construction.

The present invention for the first time provides a practical linerless tab construction which employs only a single substrate which ultimately attaches to one part or another of a diaper throughout almost all the substrate's length thereby both (1) avoiding the costs in material associated with extra lengths of substrate which bear no adhesive or bear adhesive which does not ultimately attach to one part of the diaper or another, and also (2) avoiding the costs in fabrication or handling associated with the provision of a multiple substrate construction.

Safford at column 4, lines 3-35 discusses a prior suggestion for the provision of a unitary substrate coated on one surface for half of its length with an adhesive and on the other surface for the other half of its length with another adhesive, but suggests the impracticality of such a product because of difficulties encountered in its manufacture including the problem of blocking when the tape is rolled up, and excessive costs due to waste, and problems of control and precision on rewinding.

The present invention overcomes these problems related by Safford by providing a construction in which the substrate is free of adhesive on either face at an intermediate segment or length portion which is very small in length as compared with the adhesive-bearing endward segments of the substrate, and in which release means are associated with the endward segments and the intermediate segment in such a way as to provide adequate tolerances for misalignments of the coated substrate when it is self-wound. In a preferred method of manufacture, the adhesive associated with one of the endward segments is designed to transfer upon self-winding and subsequent unwinding of the coated substrate, this being done while accommodating any slight misalignments that might occur during winding.

The result is a construction which can be manufactured very economically by fabricating operations performed on a single substrate while maintaining material costs at a minimum.

In the drawings

FIG. 1 is a diagramatic side elevation of a diaper tab contemplated by the present invention.

FIGS. 1A and 1B are similar views illustrating two possible slight variances in configuration which may occur as a result of slight variances in manufacture.

FIG. 2 illustrates the tab of FIG. 1 in folded condition in association with part of a diaper.

FIG. 3 illustrates the same tab in unfolded condition in fastening relationship between two separate parts of the diaper.

FIG. 4 illustrates in cross section half of a roll of diaper tab stock in association with a core on which it is wound.

The tab 10 shown in FIG. 1 includes a substrate 14 extending along first and second endward length portions 11 and 12 and an intermediate third length portion 13 between the length portions 11 and 12. The substrate 14 bears first adhesive 15 on its top side along the first length portion 11 and also bears second adhesive 16 on its bottom side along the second length portion 12. The substrate is free of adhesive on each side along the intermediate third length portion 13.

FIG. 1 also illustrates the configuration of the cross section of the diaper tab stock from which the illustrated tab is formed, the machine direction of such diaper tab stock extending from foreground to background in FIG. 1. Thus the first, second and third length portions 11, 12 and 13 extend transversely to machine direction.

The first length portion 11 bears release means or a release coating 17 on its bottom side which also extends partially across the intermediate third length portion 13 toward the adhesive 12 but stops short of the adhesive 12 to define a gap 19 on the bottom of the third length portion 13. The gap 19 bears no release means.

The second length portion 12 bears release means or a release coating 18 on its top side which may extend into the intermediate third length portion 13 or substantially entirely across such portion as illustrated. The latter alternative may be easily avoided if it entails any difficulty in achieving patterning accuracy sufficient to allow the release coating 18 to extend into immediate adjacency with the adhesive 15 without overlap and a consequent adhesive peeling problem. Instead the release coating 18 may be patterned to fall short of the adhesive 15, the amount of the shortfall varying from a small part of the intermediate length 13 to all or substantially all of such intermediate length, providing that the latter does not encounter a problem of blocking of another layer of adhesive 16, positioned above coating 18 when the construction is self-wound, due to unwanted absence of the coating 18 because of patterning inaccuracy (rather than the opposite problem of blocking of the adhesive 15 due to unwanted presence of the coating 18 because of patterning inaccuracy). If desired the release coating 18 may be extended part way across the length portion 13 to terminate at the same lengthwise position as the termination of the release coat 17, thus maximizing the average distance of the termination of coating 18 from the terminations of the layers of adhesives 15 and 16 which falls on either side of the termination of coating 18.

The tab 10 may be associated with a diaper portion 21 by the diaper manufacturer in the manner shown in FIG. 2. The tab 10 may either project somewhat over the edge of the diaper portion as illustrated or it may be located somewhat further inward of the diaper edge so that there is no projection. In this condition the first adhesive 15 is releasably supported on the release coating 18. The top half of the folded tab may be pulled out or extended to the position shown in FIG. 3 by a person applying the diaper, and the first adhesive may be applied to another diaper portion 22. Meanwhile the adhesive 16 remains attached to the diaper portion 21. The single substrate 14 thus is attached to one portion or the other of the associated diaper throughout almost all of the substrate's length, excepting only the very small intermediate length portion 13 labeled in FIG. 1.

In a presently preferred method of manufacture, a continuous strip of the substrate 14 is coated with release coats 17 and 18 in the manner illustrated in FIG. 1 and first and second adhesives 15 and 16 are coated in spaced relationship to each other on the top face of the substrate 14, the adhesive 15 adhereing permanently to the substrate 14 and the second adhesive 16 being releasably supported on the release coating 18. The coated substrate is then self-wound on a core 25 with the adhesive coated face or upper face on the inside of the winding as illustrated in FIG. 4. The winding and subsequent unwinding of the roll causes each turn of adhesive 16 to transfer from the release coat 18 on which it is originally releasably supported to the uncoated bottom side of an adjacent second length portion of an adjacent turn of the self-wound stock (or to the winding core, or a liner or the like located on the winding core, in the case of the innermost turn).

Slight misalignments occurring upon self-winding are readily accommodated. To illustrate this, several turns of the roll seen in FIG. 4 are labeled with the same reference numerals as the corresponding tabs 10, 10a and 10b of FIGS. 1, 1A and 1B. It will be seen that in going from turn or tab 10 to 10a the gap 19 of FIG. 1 is reduced to a smaller gap 19a labeled in FIG. 1A and also discernable in FIG. 4 although unlabeled in that Figure to avoid obscuring the illustration. If the misalignment is in the opposite direction, as for example between turns 10a and 10b in FIG. 4, then the resulting tab 10b shown in FIG. 1B will have an enlarged gap 19b. The adhesive 16 may also protrude slightly over the end of the substrate 14 as shown which does not interfere with proper operation of the diaper tab. As can be seen from FIG. 4, the first and second adhesives 15 and 16 do not block even the substrate 14 is considerably misaligned during winding. Furthermore misalignment in one direction would not cause adhesive 16 to overlap release coating 17 until the misalignment were so severe that the gap 19a was reduced to zero which would not occur unless the adhesiveless intermediate length portion 13a (FIG. 1A) were reduced to half of the magnitude of adhesiveless intermediate length portion 13 (FIG. 1), and misalignment in the opposite direction would not cause adhesive 15 to extend off the release coat 17 of an adjacent turn unless the resulting enlarged adhesiveless third length portion 13b (FIG. 1B) became fully half again as long as adhesiveless intermediate third length portion 13 (FIG. 1)

The first and second adhesives 15 and 16 may be pressure-sensitive adhesives of the same or different compositions.

The roll seen in FIG. 4 can be supplied to a diaper manufacturer who unwinds the roll, folds it lengthwise preferably along the junction between the first and third length portions, severes the stock transversely to form individual folded tabs such as seen in FIG. 2, and applies the folded tabs to diapers. It is to be noted that while the stock is wound the release coat 18 acts as a releasable support for adhesive 16 originally coated thereon and then transferred therefrom, and in the folded configuration shown in FIG. 2 the same release coating 18 acts as a releasable support for the adhesive 15 associated with the folded-over end of the tab.

The invention is not limited to the specific constructions and sequences illustrated, but is defined by the following claims.

What is claimed is:

1. A web construction of linerless diaper tab stock made up of initially flat but flexible layers suitable to be formed in long passes along the machine direction of a coating and laminating line and to be self-rolled for storage and shipment, and unrolled for use by diaper manufacturers, and fabricatable completely by web coating and slitting operations and without the necessity for folding or web-to-web fastening operations, and suitable for high speed dispensing on automatic equipment, including a substrate extending, transversely to machine direction, along first and second endward length portions and an intermediate third length portion between the other two, the substrate bearing first adhesive on its top side along the first length portion, the substrate bearing second adhesive on its bottom side along the second length portion, the substrate being free of adhesive on each side along the intermediate third length portion, said first length portion bearing release means on its bottom side for releasably supporting adhesive, corresponding to said first adhesive, that is associated with an adjacent wrap when the web construction is self-wound, said last-named release means extending partially across said intermediate third length portion toward the adhesive on said second length portion but stopping short thereof to define a gap on the bottom of said third length portion which gap bears no release means, said second length portion bearing release means on its top side for releasably supporting said first adhesive when tabs have been formed from said stock and said first length portion is folded back over said second length portion.

2. A web construction as in the foregoing claim, said release means on said second length portion extending at least partially onto said intermediate third length portion toward the adhesive on said first length portion.

3. A web construction as in claim 1, last-named release means also constituting means for releasably supporting adhesive, corresponding to said second adhesive, that is permanently associated with an adjacent wrap when the web construction is self-wound.

* * * * *